United States Patent
Borchard et al.

(10) Patent No.: US 7,044,932 B2
(45) Date of Patent: May 16, 2006

(54) IMPLANTABLE DRUG PUMP ACCESS TEMPLATE

(75) Inventors: Craig Frederic Borchard, Mendota Heights, MN (US); Michael Hexiang Zhu Drew, Maple Grove, MN (US); Jeffrey Richard Bennett, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 95 days.

(21) Appl. No.: 10/274,783

(22) Filed: Oct. 18, 2002

(65) Prior Publication Data

US 2004/0078000 A1    Apr. 22, 2004

(51) Int. Cl.
A61M 5/00    (2006.01)

(52) U.S. Cl. .................................... 604/116
(58) Field of Classification Search ............... 604/116, 604/890.1, 891.1, 892.1, 189, 190, 115, 51, 604/180, 175, 93.01, 65, 66, 67; 128/DIG. 12, 128/DIG. 13

See application file for complete search history.

(56) References Cited

U.S. PATENT DOCUMENTS

| | | | | |
|---|---|---|---|---|
| 3,650,393 A | * | 3/1972 | Reiss et al. ................ | 206/229 |
| 3,728,184 A | * | 4/1973 | Burke et al. ................ | 156/73.1 |
| 4,013,080 A | * | 3/1977 | Froning ................. | 604/165.01 |
| 4,286,584 A | * | 9/1981 | Sampson et al. ............ | 128/899 |
| 4,439,188 A | * | 3/1984 | Dennehey et al. .......... | 604/534 |
| 4,721,509 A | * | 1/1988 | Craggs .................... | 623/14.13 |
| 4,969,873 A | * | 11/1990 | Steinbach et al. ...... | 604/288.02 |
| 5,236,417 A | * | 8/1993 | Wallis ...................... | 604/82 |
| 5,281,199 A | * | 1/1994 | Ensminger et al. .... | 604/288.03 |
| 5,289,919 A | * | 3/1994 | Fischer ................... | 206/571 |
| 5,328,465 A | | 7/1994 | Kratoska et al. | |
| 5,328,466 A | * | 7/1994 | Demark .................... | 604/189 |
| 5,435,448 A | * | 7/1995 | Kempen .................... | 206/370 |
| 5,527,277 A | * | 6/1996 | Ensminger et al. ......... | 604/116 |
| 5,620,419 A | * | 4/1997 | Lui et al. ................... | 604/116 |
| 5,692,642 A | * | 12/1997 | Brattesani ................... | 222/1 |
| 6,132,416 A | * | 10/2000 | Broselow ................... | 604/506 |
| 6,293,922 B1 | | 9/2001 | Haase | |
| 6,540,756 B1 | * | 4/2003 | Vaughan .................... | 606/116 |
| 2002/0156361 A1 | * | 10/2002 | Popowski et al. .......... | 600/407 |

OTHER PUBLICATIONS

Product Brochure: "SynchroMed® Infusion System", Medtronic, Inc. (1995).
Physician's Manual: "Infusaid® Implantable Drug Delivery Systems", Shiley Infusaid Inc. (1987).

* cited by examiner

*Primary Examiner*—Manuel Mendez
(74) *Attorney, Agent, or Firm*—Eric R. Waldkoetter; John W. Albrecht

(57) ABSTRACT

An implantable drug pump and an access template for locating the implanted pump refill septum, also known as a refill port, or cathether access port are disclosed. The access template comprises a denial surface, an access port, and template labeling. The denial surface has a periphery with a location diameter and an alignment feature. The denial surface is configured to prevent penetration through a dermal layer into the implantable drug pump. The access port carried on the denial surface is configured to permit penetration through the dermal layer. The template labeling uses a label color that is substantially the same color as needle labeling color for a needle sheath covering a needle that is intended to access an implantable drug pump. The access template can be configured into a wide variety of apparatus and method embodiments.

7 Claims, 11 Drawing Sheets

US 7,044,932 B2

IMPLANTABLE DRUG PUMP ACCESS TEMPLATE

RELATED APPLICATION

This disclosure is related to the following co-pending application entitled "Catheter Access Port Denial Device" by Williamson et al. application Ser. No. 10/014,634 filed Oct. 22, 2001, which is not admitted as prior art with respect to the present disclosure by its mention in this section.

FIELD OF THE INVENTION

This disclosure relates to a template used in conjunction with an implantable medical device such as a drug pump.

BACKGROUND OF THE INVENTION

The medical device industry produces a wide variety of electronic and mechanical devices for treating patient medical conditions such as pacemakers, defibrillators, neurostimulators and therapeutic substance delivery pumps. Medical devices can be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life. One type of medical device is an implantable drug pump used to treat conditions such as movement disorders, pain, and cancer and a wide variety of other medical conditions.

An implantable drug pump is defined herein as including any implantable therapeutic substance infusion device. An implantable drug pump is implanted by a clinician into a patient at a location appropriate for the therapy that interferes as little as practicable with patient activity. Typically, an infusion catheter is connected to the drug pump outlet and implanted to infuse the drug, infusate or other therapeutic substance at a programmed infusion rate and predetermined location to treat the medical condition. Reliable and accurate operation of the drug pump is important because both inadequate and unintended therapeutic substance infusion can create patient complications. In electrically powered implantable drug pumps, the period the drug pump can be implanted is often limited by factors such as battery consumption, corrosive damage, and mechanical wear. The relatively large size of some implantable drug pumps can limit locations where the device can be implanted in a patient. An example of an implantable drug pump is shown in the Medtronic, Inc. "SynchroMed® Infusion System" Product Brochure (1995).

Many drug pumps are configured, so the pump can be replenished with drug through the septum of a refill port while the pump is implanted, so the period the pump can be implanted may not be limited by drug capacity. This is commonly done by injecting a hypodermic needle through the skin and into the septum thereby providing access to refill the reservoir. In such devices a catheter access port is often provided in addition to the refill port. The catheter access port is also accessible percutaneously by hypodermic needle. Its septum provides direct access to the catheter bypassing the pump and allows a bolus of drug or fluid medication to be administered directly into the body at the site of the catheter. The catheter access port can also be used as a diagnostic tool to troubleshoot the catheter or infusion problems. An example of an implantable drug pump having a catheter access port is shown in U.S. Pat. No. 6,293,922 "Apparatus And Method For Guiding And Limiting Access By Hypodermic Needles To Septum Of A Human Implantable Medical Treatment Device" by Haase (Sep. 25, 2001).

Implantable drug pumps often require occasional access, usually with a needle, to replenish drug or inject drug into a catheter access port. To aid in the location of the hidden septum in an access port, palpation or a template can be used.

Use of a template can help avoid some of the common problems associated with accessing a hidden access port. For example, missing the port will require the patient endure multiple needle sticks. A template can minimize the need to use radiological instruments to guide the clinician's insertion of a needle into an access port. Additionally, hitting the surface of the device can cause the sharp (but thin) point of the needle to bend, causing a burr that will make the subsequent needle stick more painful, or cause the clinician to get another needle. If the clinician is fooled into thinking they have accessed the device, she can inject the drug into the pocket, causing delivery to the wrong site in the body. Finally, the clinician can access the wrong port in the implantable device, which can have unexpected consequences. Examples of templates for implantable drug pumps as disclosed in the Medtronic Model 8551 Refill Kits and Model 8540 Catheter Access Port Kit and Pfizer Infusaid Implantable Drug Deliver System shown in the Clinician's Manual for The Infusaid Constant Flow Implantable Pump (Model 400) (1992).

BRIEF SUMMARY OF THE INVENTION

An access template for an implantable drug pump includes a denial surface 200, an access port 210, and template labeling 220. The denial surface 200 has a periphery 230 with a location diameter 240 and an alignment feature 250. The denial surface 200 is configured to prevent penetration through a dermal layer into the implantable drug pump. The access port 210 is configured to permit penetration through the dermal layer. The template labeling 220 uses a label color that is substantially the same color as needle labeling color for a needle sheath covering a needle that is intended to access an implantable drug pump. The access template can be configured into a wide variety of apparatus and method embodiments.

DETAILED DESCRIPTION OF THE INVENTION

Figure 1:
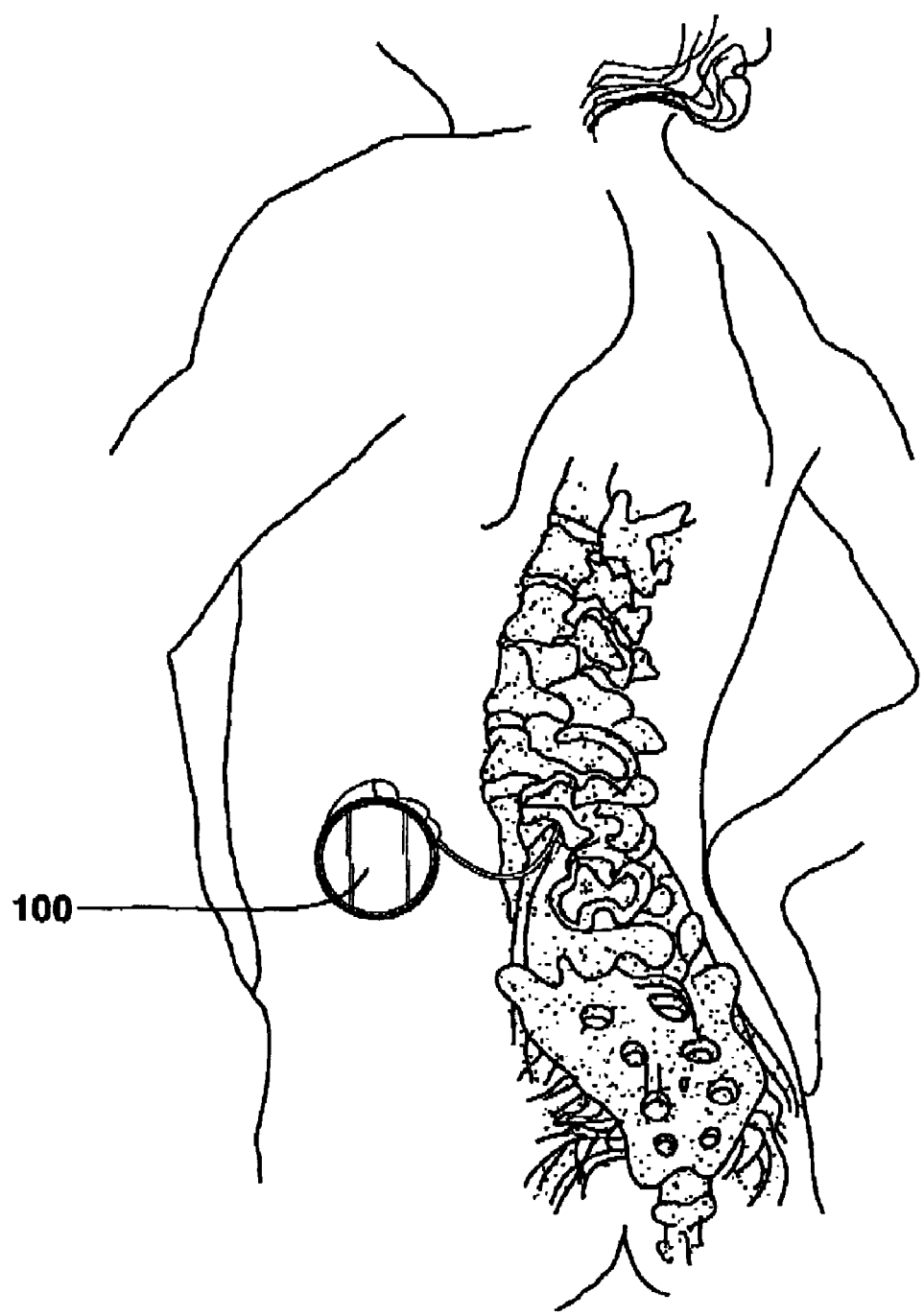
FIG. 1 shows an environmental view of an implantable drug pump embodiment.
Figure 2:
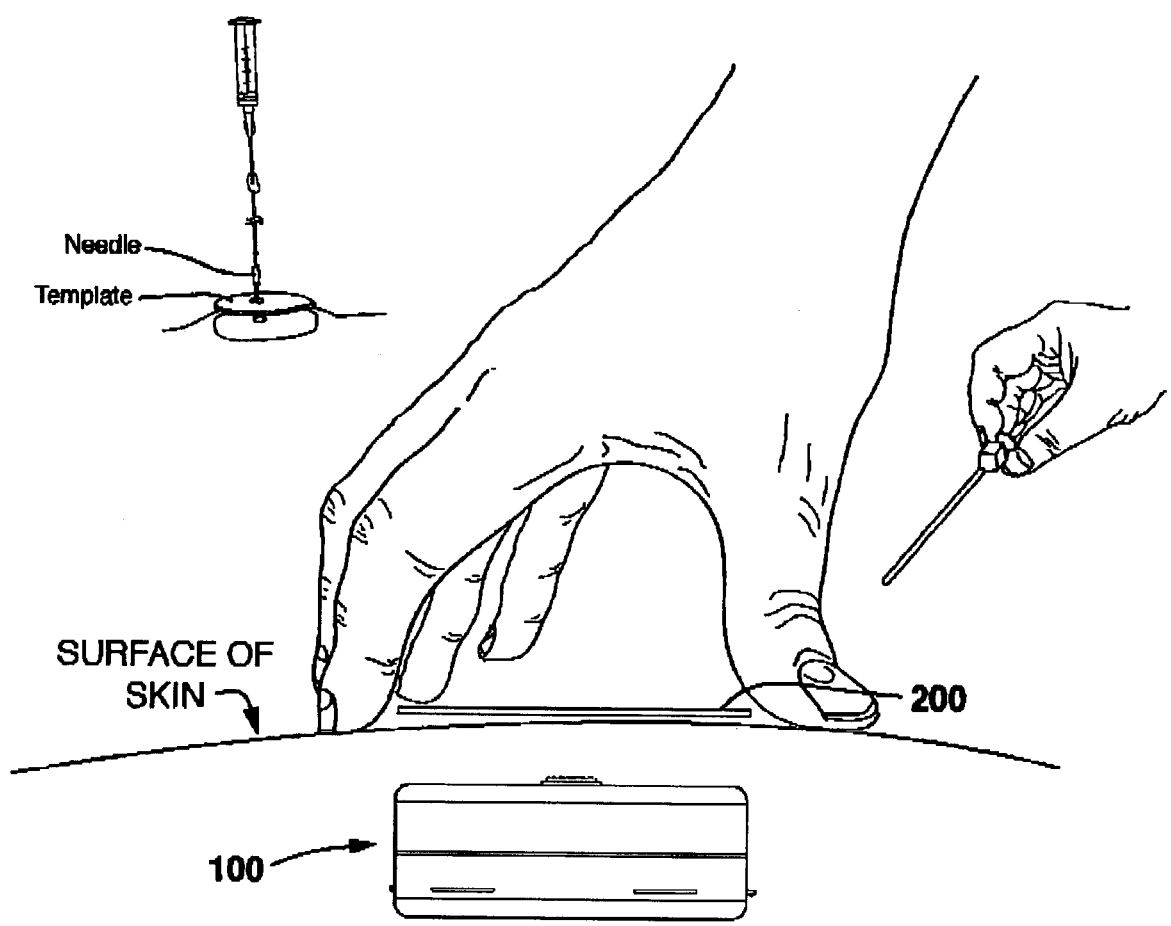
FIG. 2 shows a side view of the implantable drug pump under the surface of the skin, with the access template placed on the surface of the skin embodiment.
Figure 3:
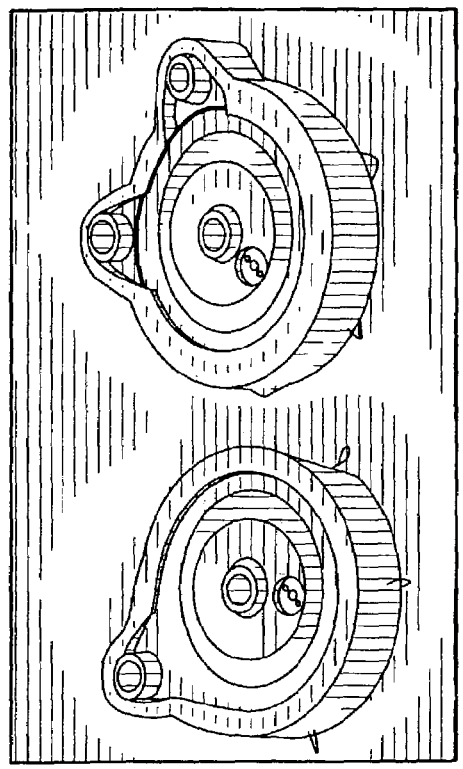
FIG. 3 shows a prior art template and an implantable pump.
Figure 3:
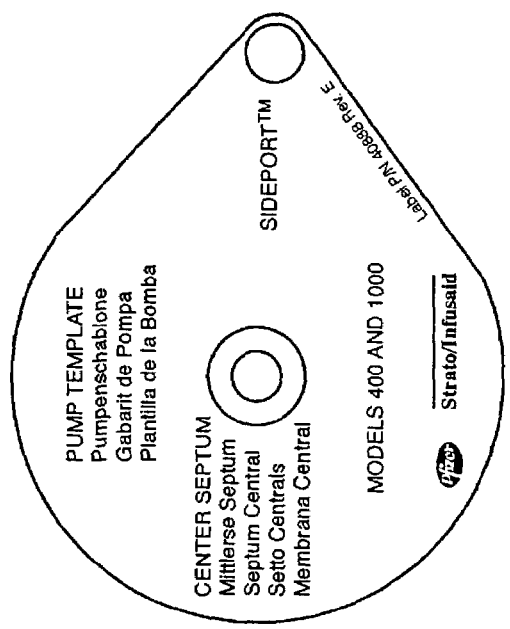

FIGS. 1 and 2 show the environment of an implantable drug pump embodiment. The implanted drug pump is located beneath the surface of the skin of the abdomen. This is often under a substantial soft, fatty tissue layer, due to the fact that it is usually preferable to secure the pump to the fascia. The implantable drug pump may be, but is not limited to, an IsoMed 110, SynchroMed 100, or SynchroMed II 120 all available from Medtronic, Inc. FIG. 3 (prior art) shows a prior art template and an implantable pump.

Figure 4:
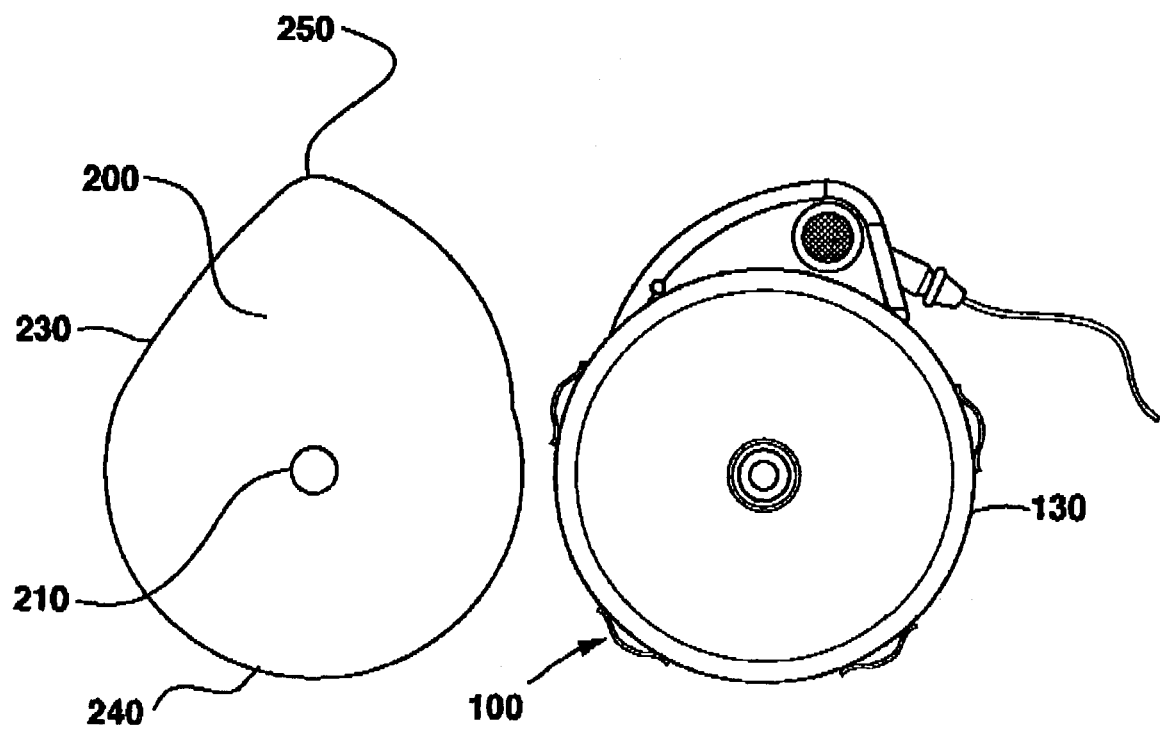
FIG. 4 shows a top view of an access template and a first implantable drug pump embodiment.
Figure 5:
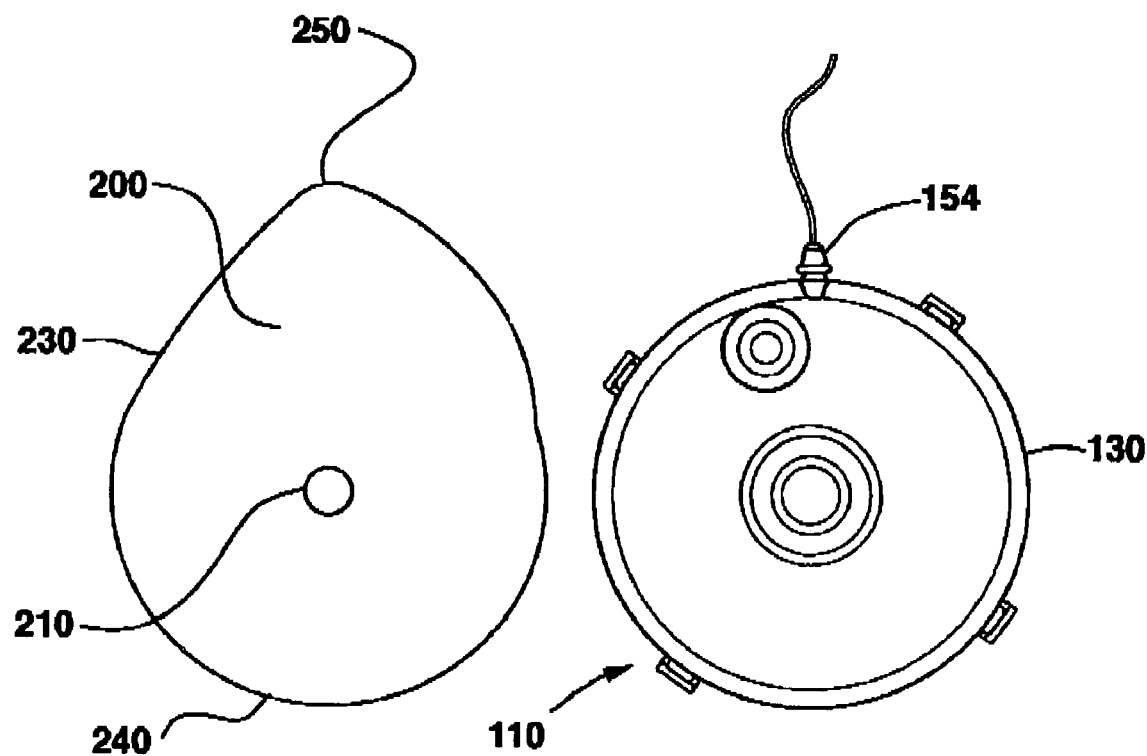
FIG. 5 shows a top view of an access template and a second implantable drug pump embodiment.
Figure 6:
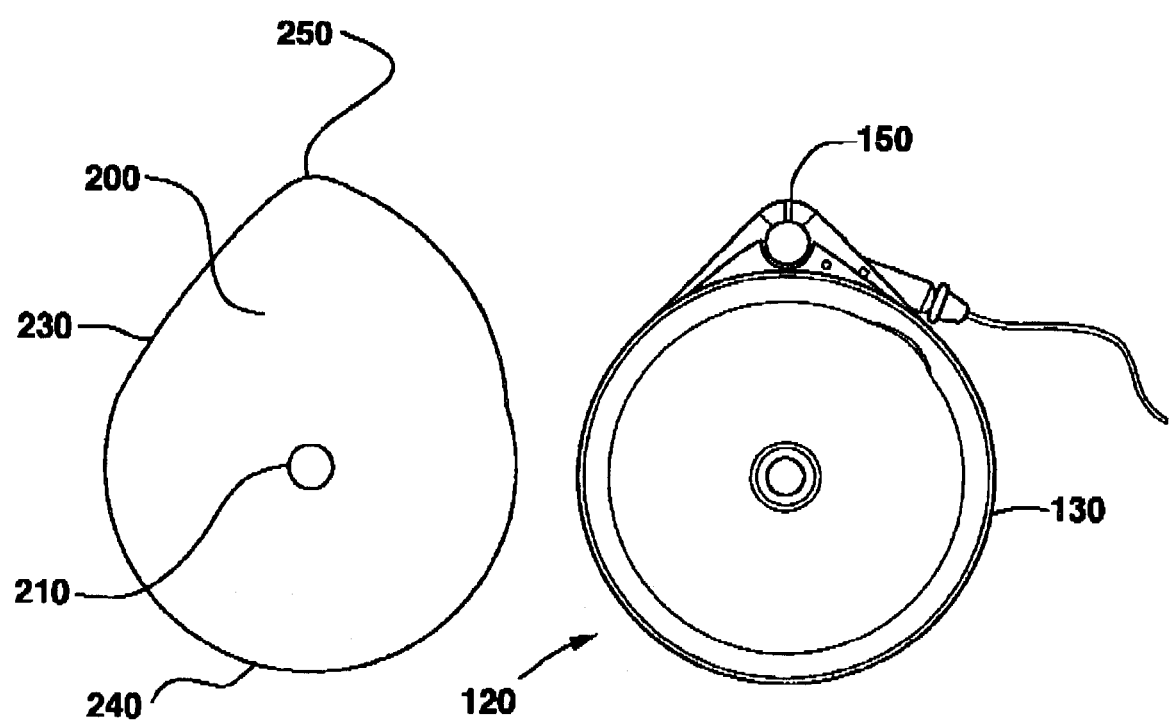
FIG. 6 shows a top view of an access template and a third implantable drug pump embodiment.
Figure 7:
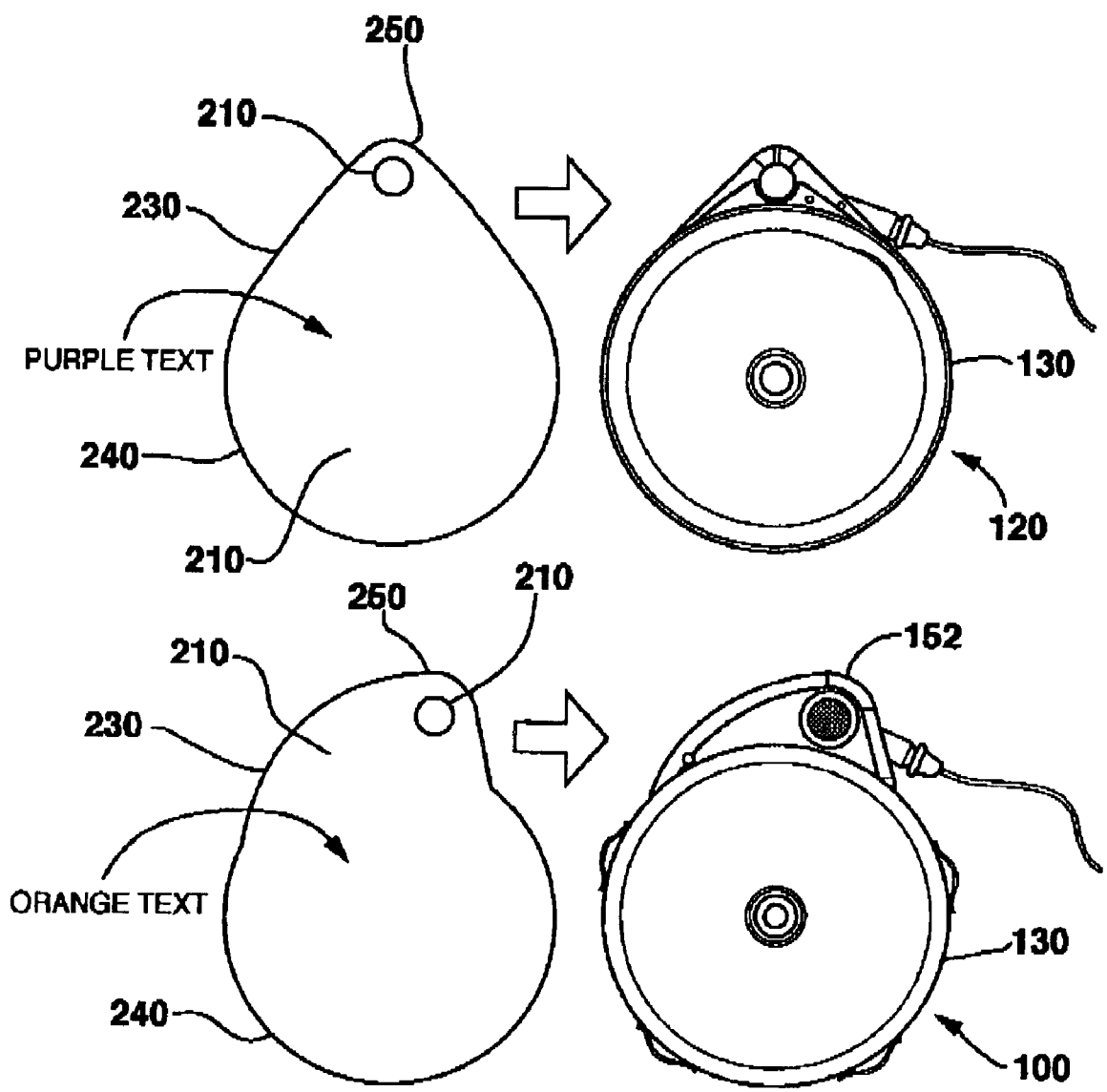
FIG. 7 shows location of two access template embodiments with the first and third implantable pump embodiments.
Figure 8:
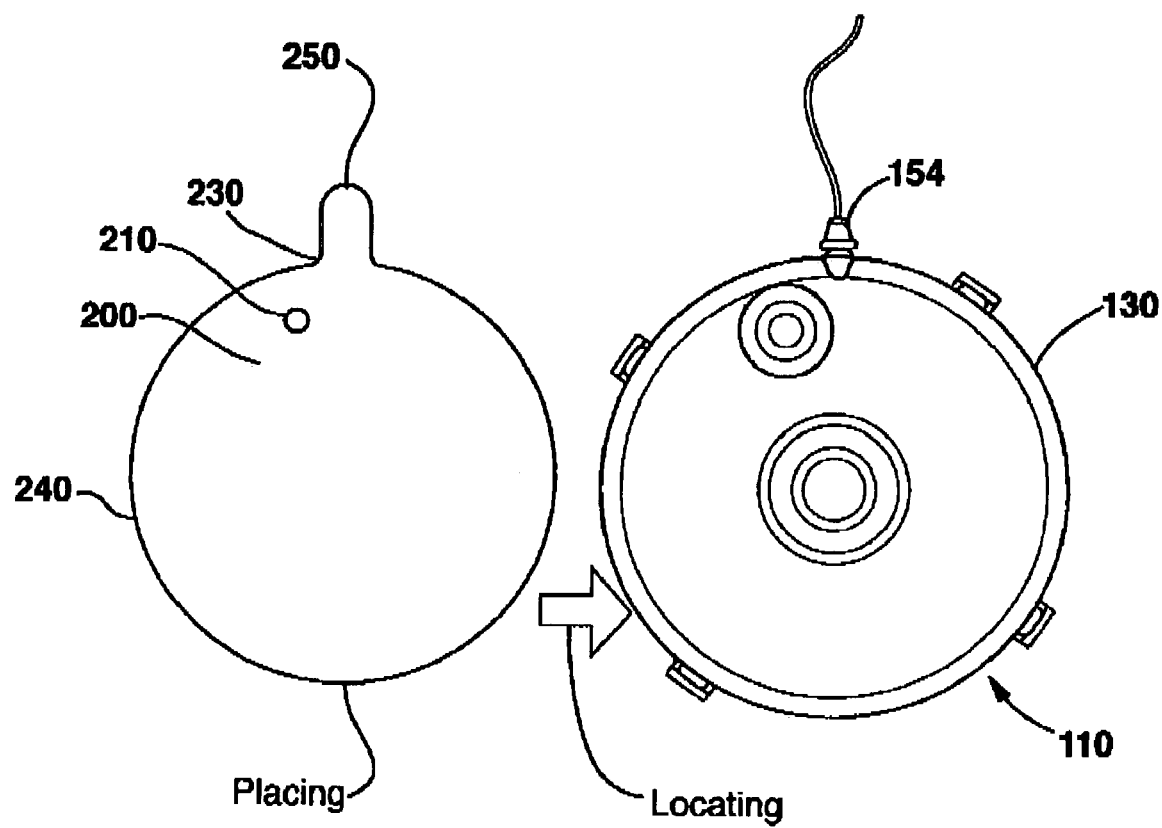
FIG. 8 shows an access template embodiment being located over the second implantable pump embodiment.
Figure 9:
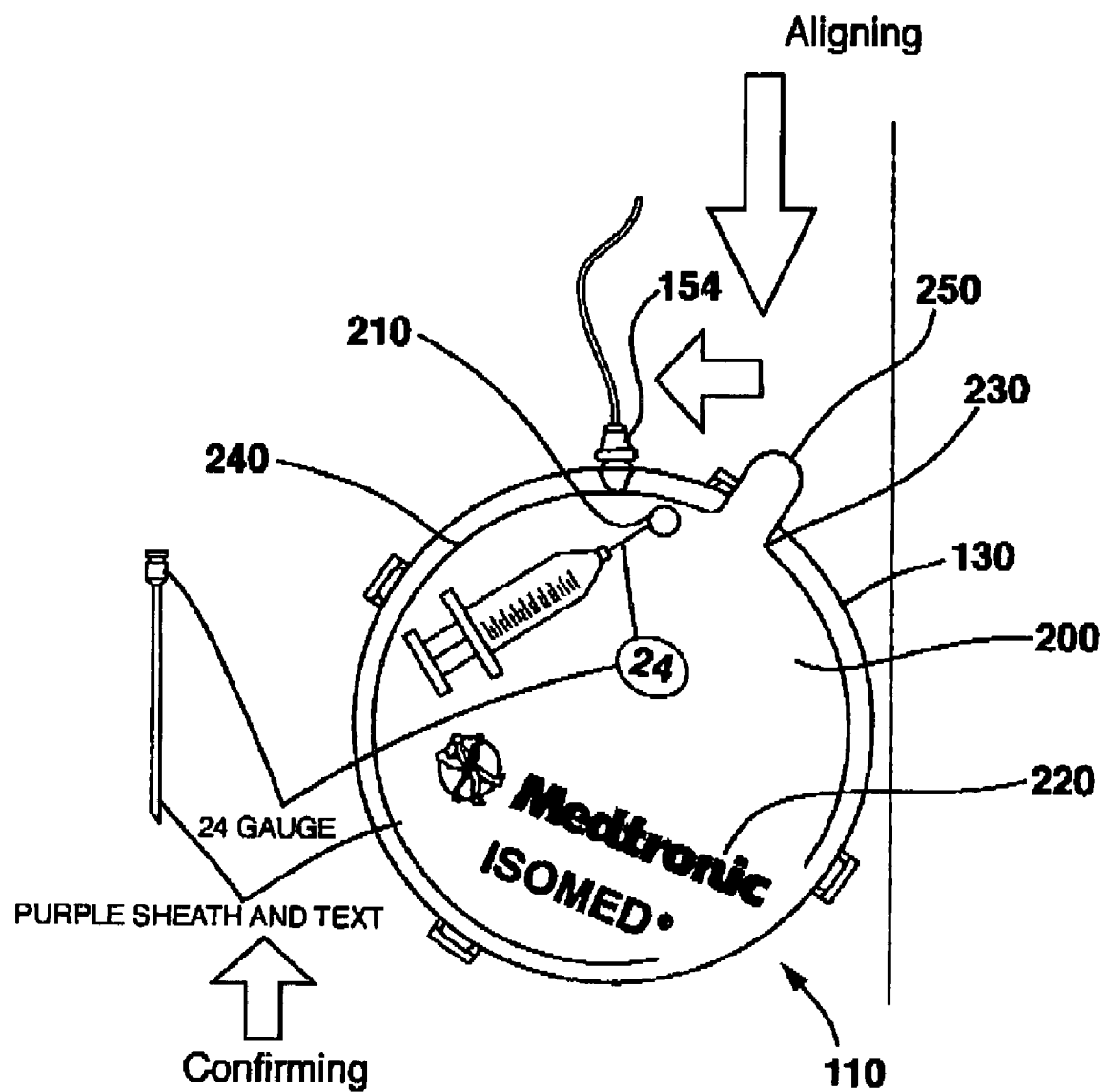
FIG. 9 shows an access template embodiment being aligned and confirmed over the second implantable pump embodiment.

FIGS. 4, 5, and 6 show an access template 260 and various implantable drug pump embodiments, and FIGS. 7, 8, and 9 show use of an access template 260 with implantable drug pumps 100, 110 and 120. An access template 260 for an implantable drug pump includes a denial surface 200, an access port 210, and template labeling 220. The denial surface 200 has a periphery 230 with a location diameter 240 and an alignment feature 250. The denial surface 200 is configured to prevent penetration through a dermal layer. A denial surface 200 may be made of polycarbonate or any other material that prevents needle penetration through the denial surface 200 and into the dermal layer. An alignment feature 250 is any detail of the denial surface 200 that indicates to the user the correct position of the template 260 over the implanted drug pump. For example, an alignment feature 250 could be deviation of the denial surface 200 from a circular shape to indicate that such deviation portion should be aligned with the portion of the drug pump that deviates from a circular shape (in those cases in which the drug pump is not perfectly circular). Another example, of an alignment feature 250 is a detail such as a protrusion on the top surface of the template 260. Certainly, other details and features and means can be contemplated that are to be considered alignment features for this invention. The access port 210 is configured to permit penetration through the dermal layer. The access port 210 can be a wide variety of access ports such as a refill port, a catheter access port, and the like. The access port 210 serves as a means for accessing a single septum carried on an implantable drug pump.

In a first embodiment, the access template 260 is designed to be a universal template. The denial surface 200 is designed to be the largest possible compared to the range of implantable drug pumps intended to be accessed, while still permitting the centering and aligning process necessary to locate the access port septum of any of the implantable drug pumps under consideration. This allows the denial surface 200 to provide maximum protection.

The template labeling 220 is carried on the denial surface 200. Template labeling 220 that is carried on an additional sheet that is attached to the denial surface 200 is considered to be carried on the denial surface 200. The template labeling 220 providing data for penetrating the access port 210. The template labeling 220 has a label color that is substantially the same color as needle labeling color for a needle hub and/or sheath covering a needle that is intended to access an implantable drug pump. The template labeling color and hub and/or sheath color can be any of a wide variety of colors that permit confirmation that an access needle is appropriate such as black, purple, orange, and the like. The template labeling 220 can include the appropriate needle size. In a second embodiment, multiple templates and needle sizes exist within the sterile tray. The color coding and labeling 220 on the denial surface 200 permit selection of the proper template 260 and needle for the given application. The indicia on the template 260 that is color coded may be any indicia. The indicia may be the serial number of the device, it may be the trademark associated with the device, it may be the company logo, it may be a picture of a needle, it may be a special colored dot or other symbol and it may be any other indicia. This invention is not limited to the color coding of only certain indicia.

Figure 10:
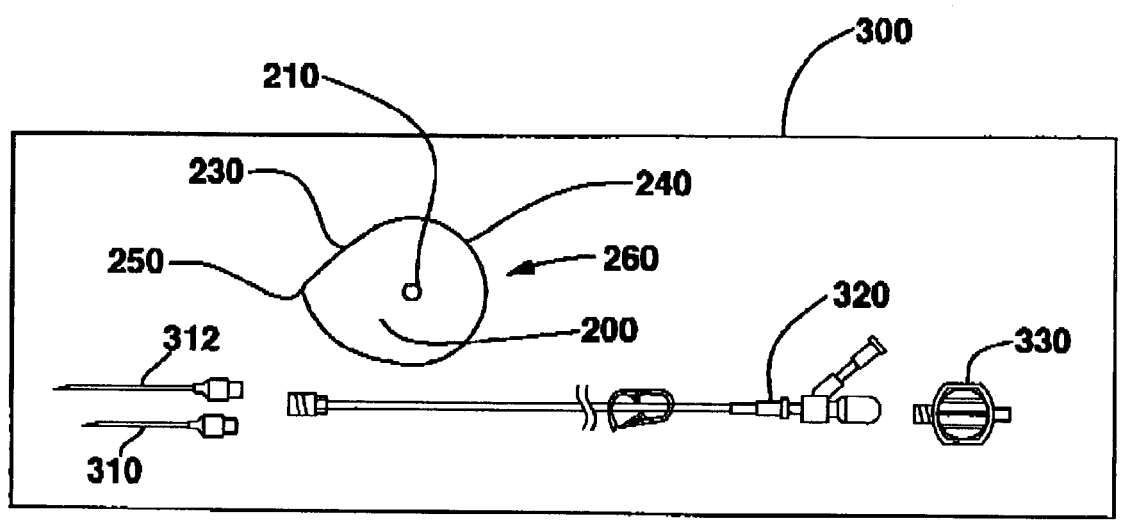
FIG. 10 shows a kit for supplying drug to an implantable drug pump embodiment.

FIG. 10 shows a kit for supplying drug to an implantable drug pump includes a sterile packing container 300, an access needle 310 and 312, an extension set 320, a filter 330, and an access template 260. There is at least one access needle 310 or 312 carried in the sterile packing container. The extension set 320 is configured to couple to the access needle 310 or 312. The filter 330 is coupled to the extension set 320. The access template 260 has an access port 210 and is configured to access a septum on an implantable drug pump. The access template 260 is described above in more detail.

Figure 11:
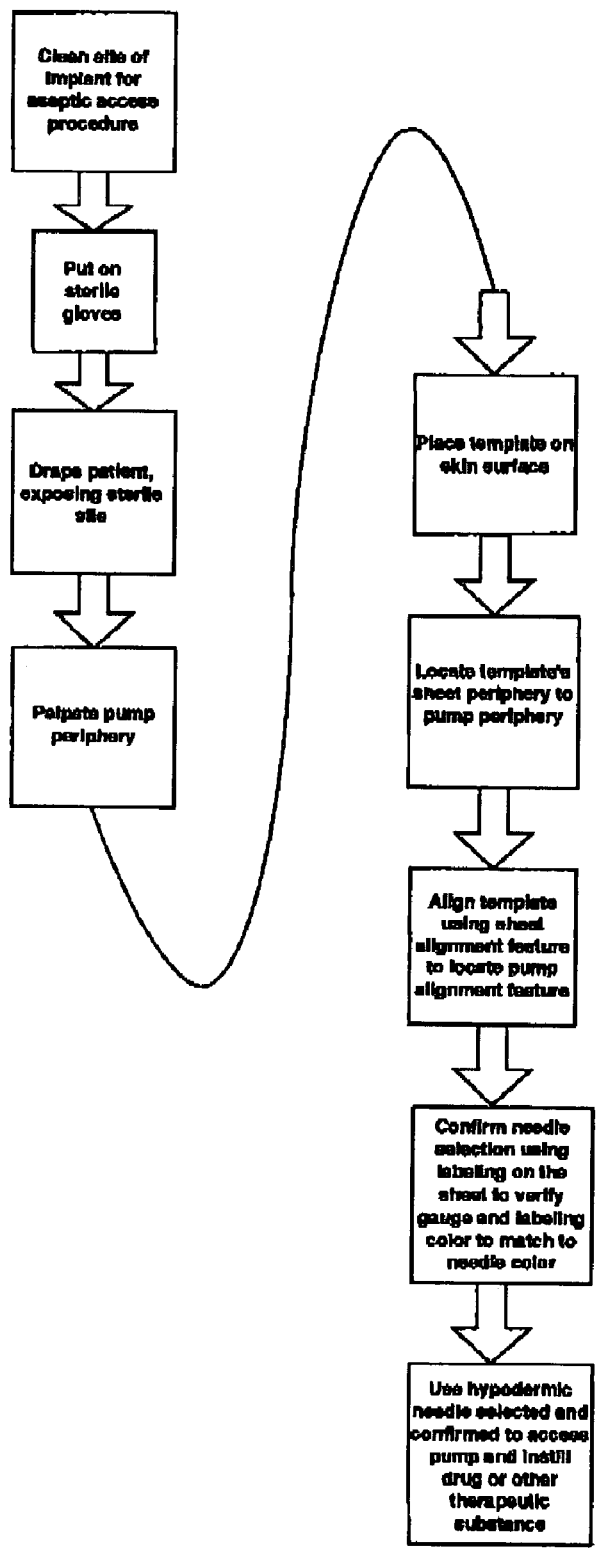
FIG. 11 shows a flow diagram of a method for accessing a single septum carried on an implantable drug pump embodiment.

FIG. 11 shows a method for accessing a single septum carried on an implantable drug pump comprises placing a template 260, locating a denial surface periphery 230, aligning an alignment feature 250, and confirming that an access needle 310 or 312 is appropriate. The pump is first identified and located. The template 260 is placed over a pump proximal side of an implantable drug pump. The denial surface periphery 230 is located with a pump periphery 130. The alignment feature 250 is aligned with a pump alignment feature 150, 152 or 154. The appropriate access needle is confirmed for a single septum by comparing template labeling 220 carried on a denial surface 200 with needle labeling. The pump is accessed with the access needle through the access port 210 on the access template 260. Fluids are removed and/or injected.

Thus, embodiments of the implantable drug pump access template are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An access template far an implantable drug pump, comprising:
    a denial surface configured to prevent penetration through a dermal layer into the implantable drug pump, the denial surface including a periphery, and a location diameter;
    an access port carried on the denial surface, the access port configured to permit penetration through the dermal layer; and,
    template labeling carried on the denial surface, the template labeling having a label color that is substantially the same color as needle labeling color for a needle sheath covering a needle that is intended to access an implantable drug pump.

2. The access template as in claim 1 wherein the template labeling color and sheath color are selected from the group consisting of black, purple, and orange.

3. The access template as in claim 1 wherein the template labeling includes the appropriate needle size.

4. The access template as in claim 1 wherein the access port is selected from the group consisting of a refill port and a catheter access port.

5. The access template as in claim 1 wherein the denial surface further comprises an alignment feature.

6. An access template for an implantable drug pump, comprising:
   a denial surface configured to prevent penetration through a dermal layer, the denial surface including a periphery and a location diameter; and,
   means for accessing a single septum carried on an implantable drug pump using template labeling carried on the denial surface, the template labeling having a label color that is substantially the same color as needle labeling color for a needle sheath covering a needle that is intended to access an implantable drug pump.

7. A kit for supplying drug to an implantable drug pump, comprising:
   a sterile packing container;
   at least one needle carried in the sterile packing container, the needle having a needle sheath;
   an extension set configured to couple to the access needle;
   a filter coupled to the extension set; and,
   an access template having an access port configured to access a single septum on an implantable drug pump and template labeling, the template labeling having a label color that is substantially the same color as needle labeling color for the needle sheath covering the needle.

* * * * *